United States Patent
Schwartz et al.

(10) Patent No.: US 10,118,016 B2
(45) Date of Patent: Nov. 6, 2018

(54) MICROVASCULAR OBSTRUCTION DETECTION AND THERAPY

(71) Applicant: OSPREY MEDICAL, INC., Minnetonka, MN (US)

(72) Inventors: Robert S. Schwartz, Inver Grove Heights, MN (US); Robert A. Van Tassel, Excelsior, MN (US)

(73) Assignee: Osprey Medical, Inc., Minnetonka, MN (US)

( * ) Notice: Subject to any disclaimer, the term of this patent is extended or adjusted under 35 U.S.C. 154(b) by 24 days.

(21) Appl. No.: 15/256,272

(22) Filed: Sep. 2, 2016

(65) Prior Publication Data

US 2016/0367785 A1 Dec. 22, 2016

Related U.S. Application Data

(63) Continuation of application No. 13/759,431, filed on Feb. 5, 2013, now Pat. No. 9,433,761, which is acontinuation of application No. 12/376,086, filed as application No. PCT/US2007/075002 on Aug. 1, 2007, now Pat. No. 8,430,861.

(Continued)

(51) Int. Cl.
*A61M 25/00* (2006.01)
*A61B 5/0215* (2006.01)
*A61B 5/055* (2006.01)
*A61B 8/00* (2006.01)
*A61M 25/10* (2013.01)
*A61B 5/02* (2006.01)

(Continued)

(52) U.S. Cl.
CPC ....... *A61M 25/007* (2013.01); *A61B 5/02007* (2013.01); *A61B 5/0215* (2013.01); *A61B 5/055* (2013.01); *A61B 8/00* (2013.01); *A61B 8/06* (2013.01); *A61M 25/10* (2013.01); *A61M 25/1011* (2013.01); *A61M 37/0092* (2013.01); *A61M 2025/0002* (2013.01); *A61M 2025/0003* (2013.01); *A61M 2025/1052* (2013.01)

(58) Field of Classification Search
CPC .. A61M 2025/1052; A61M 2025/1095; A61M 2025/0002; A61M 25/1011; A61B 5/055; A61B 5/02007; A61B 8/00; A61B 5/026; A61B 5/6852

See application file for complete search history.

(56) References Cited

U.S. PATENT DOCUMENTS

| | | | |
|---|---|---|---|
| 5,807,265 A | 9/1998 | Itoigawa et al. | |
| 6,354,999 B1 * | 3/2002 | Dgany | A61B 1/015 |
| | | | 600/486 |

(Continued)

FOREIGN PATENT DOCUMENTS

| | | |
|---|---|---|
| WO | WO 2005/072409 | 8/2005 |
| WO | WO 2007/061530 | 5/2007 |

OTHER PUBLICATIONS

PCT International Search Report and Written Opinion in International Application PCT/US2007/075002, dated Jul. 16, 2008, 4 pages.

(Continued)

*Primary Examiner* — Deanna K Hall

(57) ABSTRACT

A method of detecting and treating a microvascular obstruction is provided. In one embodiment, a catheter is provided for both detecting the microvascular obstruction and treating or removing the obstruction.

9 Claims, 6 Drawing Sheets

Related U.S. Application Data

(60) Provisional application No. 60/821,216, filed on Aug. 2, 2006, provisional application No. 60/821,678, filed on Aug. 7, 2006, provisional application No. 60/864,130, filed on Nov. 2, 2006, provisional application No. 60/864,336, filed on Nov. 3, 2006.

(51) Int. Cl.
*A61B 8/06* (2006.01)
*A61M 37/00* (2006.01)

(56) References Cited

U.S. PATENT DOCUMENTS

| | | |
|---|---|---|
| 6,949,087 B2 | 9/2005 | Van Tassel et al. |
| 7,374,560 B2 * | 5/2008 | Ressemann ...... A61B 17/12045 604/509 |
| 8,430,861 B2 | 4/2013 | Schwartz et al. |
| 9,433,761 B2 | 9/2016 | Schwartz et al. |
| 2003/0149368 A1 | 8/2003 | Hennemann et al. |
| 2005/0059930 A1 | 3/2005 | Garrison et al. |
| 2005/0090748 A1 | 4/2005 | Makower et al. |
| 2005/0107738 A1 | 5/2005 | Slater et al. |
| 2005/0113798 A1 | 5/2005 | Slater et al. |
| 2005/0165354 A1 | 7/2005 | Schwartz et al. |
| 2005/0245897 A1 | 11/2005 | Bolduc et al. |

OTHER PUBLICATIONS

PCT International Preliminary Report on Patentability in International Application PCT/US2007/075002, dated Feb. 3, 2009, 5 pages.

* cited by examiner

FIG. 9
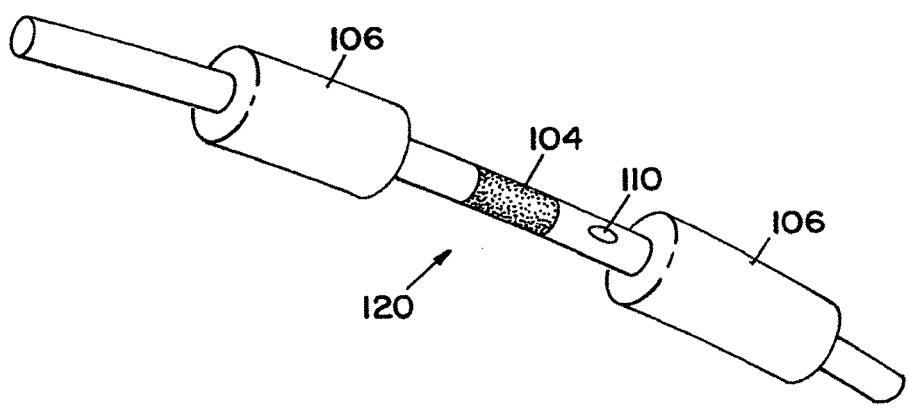
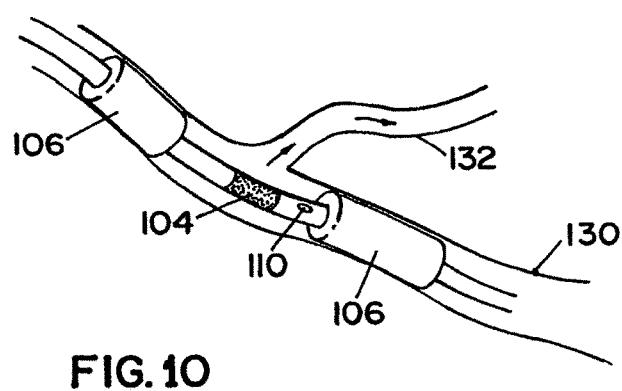
FIG. 10

MICROVASCULAR OBSTRUCTION DETECTION AND THERAPY

RELATED APPLICATIONS

This application is a continuation of U.S. patent application Ser. No. 13/759,431, filed Feb. 5, 2013, now U.S. Pat. No. 9,433,761; which is a continuation of U.S. patent application Ser. No. 12/376,086, filed Jan. 20, 2010, now U.S. Pat. No. 8,430,861; which is a national stage application of PCT/US2007/075002, filed Aug. 1, 2007; which claims priority to U.S. Provisional Application Ser. No. 60/821,216 filed Aug. 2, 2006 entitled Microvascular Obstruction Detection and Therapy; U.S. Provisional Application Ser. No. 60/821,678 filed Aug. 7, 2006 entitled Microvascular Obstruction Detection and Therapy; U.S. Provisional Application Ser. No. 60/864,130 filed Nov. 2, 2006 entitled Microvascular Obstruction Therapy III; and U.S. Provisional Application Ser. No. 60/864,336 filed Nov. 3, 2006 entitled Microvascular Obstruction Therapy; all of which are hereby incorporate by reference.

BACKGROUND OF THE INVENTION

Blockages of blood flow to the smaller blood vessels in the body, also referred to as microvascular obstruction, often result in ischemic insult and necrosis of nearby tissue. These microvessels circulate blood to almost all major organs of the body, such as the heart, kidneys, skeletal muscles, and brain, as well as to more peripheral areas such as extremities, muscles and skin. In this respect, microvascular occlusions can damage almost any area of the body, resulting in a wide range of complications and diseases.

Generally, microvascular obstruction is caused by thrombotic occlusions (e.g., platelets, fibrin or both), vasospasm of the micro vessels (i.e., sudden narrowing), leukocyte (white blood cell) or a combination of these. Due to the small size of the microvessels, typically 8-1500 micrometers in diameter, detection of obstruction remains difficult. Further, even when obstruction is localized, effective treatments can be similarly difficult to deliver.

BRIEF DESCRIPTION OF THE DRAWINGS

FIG. 9 illustrates a side view of a dual balloon detection and treatment system according to the present invention;

FIG. 10 illustrates a side view of the dual balloon detection and treatment system of FIG. 9;

DETAILED DESCRIPTION OF THE INVENTION

Figure 1:
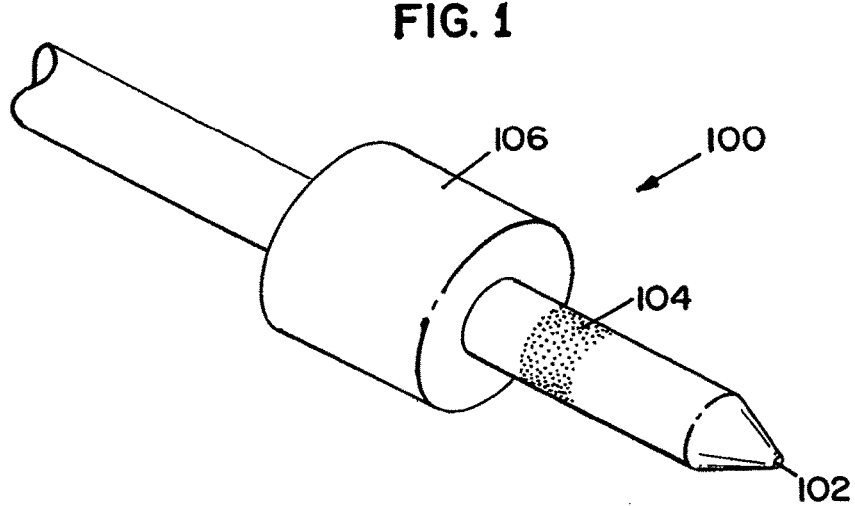
FIG. 1 illustrates a perspective view of a preferred embodiment of a detection and treatment catheter according to the present invention.

Effective treatment of microvascular obstruction ideally focuses on initially detecting the presence and specific location of an obstruction, then treating the location to remove or at least reduce the blockage. While different preferred embodiments of detection and treatment methods are discussed below, it should be understood that these techniques can be used alone, in combination with each other or in combination with other techniques not specifically disclosed in this specification.

Detection of Microvascular Obstruction

In one preferred embodiment, microvascular obstruction is detected with MRI imaging. The patient is imaged in the general location where the obstruction is thought to be. The doctor then reviews these Magnetic Resonance Imaging (MRI) Images to locate the precise position of the obstruction. Once located, the obstruction can be removed by any of the removal techniques discussed in this specification.

In one preferred embodiment, microvascular obstruction is detected by monitoring a loss or diminution of blood flow or perfusion in a focal piece of a muscle or tissue. For example, blood flow can be monitored by producing a 1 MHz ultrasonic signal from an offsite catheter or from an ultrasonic signal from a treatment catheter. Reflections of the signal are utilized to detect microvascular extraction and additionally to enhance dissolving the obstruction as discussed in further detail below.

In another preferred embodiment, microvascular obstruction is detected by measuring a wedge pressure (wedge pressure being generally defined as the intravascular pressure reading obtained when a fine catheter is advanced until it completely occludes a blood vessel, or with a small balloon used to occlude the vessel distally. For example, wedge pressure within the myocardium may be detected with a catheter having two or more pressure measuring balloons (e.g., low pressure balloons). As the myocardium contracts, it squeezes the microvasculature and likely increases the external pressure on the vessels. As this pressure increase occurs, the nearby vessels may close during systole, allowing pressure in the proximal coronary artery to be sensed over time. If the proximal vessel is partially or completely occluded by, for example, a balloon, the pressure in the vessel distal to the balloon and proximal to the myocardium will be sensed as a rhythmic rise in proportion to myocardial contraction.

When a microvascular obstruction is present, the pressure waveform is damped in amplitude, frequency, or even completely absent, depending on whether a vessel is completely or partially occluded. This pressure waveform of an occluded vessel is comparatively different from normal unoccluded microvasculature, for example, by comparing the amplitude, frequency and flow. However, the condition of the myocardial contraction will also affect this pressure waveform. As the "squeeze" damps the waveform to zero (i.e., the muscle is not contracting) the pressure waveform will be substantially damped as well. As the occlusion is improved in the micro vessel, and/or as the myocardial contraction occurs more vigorously, the waveform may, for example, increase in amplitude in a proportional manner. In this respect, the pressure measurement provides information over time regarding the success and progress of the microvascular treatment.

In this respect, amplitude, frequency and flow all find use to guide the therapy (e.g., delivery of treatment agents) of a microvascular obstruction. As the obstruction is improved and as the myocardial contraction occurs more vigorously, the pressure waveform will increase in amplitude in a proportional manner. Measuring the waveform's changes over time during treatment will yield useful information regarding the success and progress of the treatment. Further, a catheter may be placed in the myocardial venous system and a time-varying pressure waveform introduced to measure from the arterial side, also for determination of the microvasculature in a similar manner as above using the natural waveform generated as the heart muscle contracts.

In another preferred embodiment, microvascular obstruction is detected by measuring vascular impedance within a patient. Vascular impedance is generally defined as blood pressure divided by the blood flow and therefore is obtained by measuring blood pressure and blood flow (e.g., velocity or volumetric) within a vessel. Preferably, these readings are measured by inflating a balloon of a catheter within a vessel, then measuring relevant data such as pressure, flow, and volume or flow caused by the dispensed treatment agents while the balloon causes obstruction of the vessel. As multiple readings are taken from different locations within the vessel, the resulting data can be analyzed to help determine the location of the microvascular obstruction. This reading may occur in 'real time' as the fluid, which may contain therapeutic agent or agents, is injected into regions of microvascular obstruction.

Figure 12:
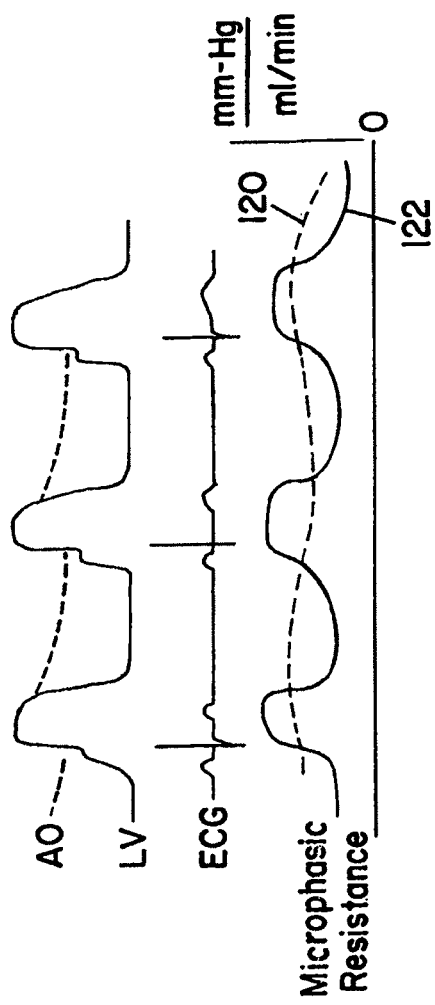
FIG. 12 illustrates a graph of phasic flow according to a preferred embodiment of the present invention.

The nature of a microvascular obstruction is such that it augments phasic resistance 122, seen in FIG. 12, and hence measuring phasic pressure amplitude, direction, and phase timing can indicate both the initial severity of the microvascular obstruction and the response to the therapy. More specifically, the microvascular thrombus or other occluding matter fill is incomplete during an obstruction and therefore phasic squeezing of the coronary microvessels by myocardial contraction creates a phasic antegrade pressure that can be measured. In cases of severe microvascular occlusion, contrast exhibits phasic flow and may be pumped in a retrograde direction during myocardial systole since this retrograde flow is blocked by the obstruction.

With myocardial contraction, it is likely that the resistance parameter (pressure/flow, or by dimensions, mmHg/ml-min) is a useful absolute and relative marker of MVO and proportional in severity. Infusion of fluid at a constant flow rate can cause phasic variation in distal catheter pressure during myocardial systole. The pressure can be measured in the flow scenario and an estimated of MVO severity obtained. This distal resistance creates an accurate, real-time method to measure such resistance. Further, this resistance is phasic and the parameters of the phasicity can determine the severity of the MVO.

The mean 120 (also in FIG. 12) of the phasicity or other derived waveform from the phasicity may also be processed for determining alternative parameters of the MVO severity. This concept uses a non-constant, varying parameter to measure or process and derive a physiological number related to an MVO parameter.

Treatment of Microvascular Obstruction

In one preferred embodiment according to the present invention, treatment of a microvascular obstruction is achieved by dissolving the emboli by delivering one or more treatment agents to the obstruction (e.g., with a balloon treatment catheter described elsewhere in this specification). This combination of fluids may be simultaneous as in a mixture, or as separate injections. Since these obstructions or emboli are typically composed of platelet/fibrin emboli, dissolution is effectively achieved, in one example, by a multifactorial approach that includes inhibition of the intrinsic, extrinsic and platelet "disaggregation". In a more specific example, a combination of glycoprotein IIB/IIIA inhibition, direct thrombin inhibition, indirect thrombin inhibition, and a clotting factor such as Factor X, Factor VII, or other factors in this clotting pathway can be used. In another more specific example, a combination of argatroban, any IIB/IIIA agent, Tick Anticoagulant Peptide, echistatin, Integrilin, PPACK, and DPG peptide inhibitor can be delivered to an occlusion.

Additionally, a traditional fibrinolytic agent such as TNK, streptokinase, urokinase, or rTPA may also be included, as well as antispasmotic agents such as adenosine, nitroglycerin, sodium nitroprusside, nicorandil or similar agents capable of relieving micro or macrovascular spasm. Further examples of treatment agents include Hirulog, Bivalrudin, ReoPro, eptifibatide, TAP, Heparins, LMW Heparins, Argatroban, Hirudin, Refludan/Lepirudin (Berlex), Desirudin, Recombinant forms, ABCIXIMAB, Eptifibatide, Tirofiban, Alteplase, Reteplase, Tenecteplase, Factor Xz, rivaroxaban, and Fodaparinux.

Additional treatment agents may include agents active against accumulation of polymorphonuclear leukocytes. Inhibition of these cells will be myocardial protective. Specific examples may include anti-inflammatory agents, adenosine, anti-PMN antibodies, anti-leukocyte antibodies, quinolone agents, nitrogen mustard, and hydroxyurea. Further treatment agents may include anti-serotonin agents, such as cinanserin, pizotifen, cyproheptadine, lysenyl, mianserin, methysergide, promethazine, octreotide, and others.

In another example, intermediate and older clots are treated with enzymes known to be more effective in treating these types of obstruction, such as trypsin, papain, chymotrypsin and similar proteolytic agents. These agents are preferably infused under pressure at a microvascular obstruction to drive the agents into the obstruction to enhance efficacy against the obstruction.

More specifically, the treatment agents can be delivered locally into the microvasculature via catheter placed into the larger surrounding vessels, then diffusing these agents, either alone or under pressure with balloon occlusion. Alternately, these agents may be injected retrograde to the coronary venous system where the obstruction can be dissolved. Often, the obstruction is quite porous and will accept diffusion of a treatment agent or series of agents when dissolved in a solution such as water or saline.

This infusion pressure is preferably gated with the ECG waveform, providing the highest pressure as the heart is relaxing and the lowest when the heart is contracting, thereby infusing the micro vessels at their most receptive time in the cardiac cycle. Alternately, the pressure function/waveform may be other than a constant pressure and may be periodic, possibly though not necessarily gated to the cardiac cycle. For example, the function/waveform may be a pulse, square wave, sinusoidal, or other non-constant pressure waveform. The contour of the waveform at the tip of the treatment catheter is a function of the peripheral resistance and serves as a diagnostic technique.

The treatment agents may further include anti-arrhythmic agents to prevent or limit reperfusion arrhythmias. For example, class I, II, and III anti-arrhythmia agents can be used, as well as lidocaine, quinidine, amiodarone, procainamide, propofenone, and beta blockade.

The treatment agents delivered to the microvascular obstruction may further include agents to restore microvascular integrity and limit capillary leakage. Preferably, these agents may act to limit capillary access by coating the surface of the microvascular lumen. For example, a protein or other weight carbohydrate infusion including albumin or LMW Dextran can be used. These agents may be oxygenated to enable more prolonged infusion. Further, antibody coatings may also be included to prevent cellular demargination, such as CD 18 (anti-), or to attract healthy cells such as CD 133 or CD 34 positive cells.

The treatment agents may further include agents that are known to those skilled in the art to produce electrical or mechanical arrest of tissue surrounding the microvascular obstruction to prevent damage due to poor blood flow. Generally, use of such agents will temporarily halt or significantly limit metabolic activity to prevent arrhythmias and limit energy consumption and therefore energy needs for the infracted region. Preferably, application of these agents are delivered to the tissue area downstream of the microvascular obstruction, placing this tissue in a temporary "sleep" until the obstruction can be cleared and normal blood flow returned to the tissue area.

Lysis of the obstruction is optionally detected or further confirmed by an inline sensor on a delivery catheter that detects small particulate matter. Preferably, this emboli sensor provides real-time lytic activity which allows a user to collect lytic material and/or treatment drugs at an appropriate time (i.e., as the emboli is dissolving) to prevent their release into the patients circulatory system. For example, a catheter may include a sensor that detects light refraction, reflection or transmission. In this example, particles scatter light in a specific fashion and therefore indicate that lysis has occurred. Once the sensor has detected that lysis has occurred, the user can quickly remove (e.g., suction out) any of the embolic particles and treatment agents to prevent unintentional damage to other areas of the circulatory system.

Alternately, the pressure at the distal end of the catheter can be similarly monitored so that when a drop in pressure is detected (i.e., the obstruction is broken up or dissolved) the user can immediately stop injecting treatment agents to the vessel and suction out any remaining debris or treatment agents.

While the liquid containing the thrombotic components and treatment agents can be permanently removed from the patient, this liquid can alternately be returned to circulation after filtration of the unwanted materials (such as chemicals and proteins), returning only the desired portions of the liquid (e.g., red blood cells, white blood cells and platelets). For example, the liquid can be filtered through a porous filter membrane by centrifugal or mechanical force which allows the smaller protein and chemical particles to pass through while holding the larger blood cells.

In another preferred embodiment, the microvessels are constricted (including those that are patent), with vasoconstricting agents for example (e.g., norepinephrine, epinephrine, dopamine, phenylenphrine, alpha agonists, and caffeine), prior to treatment of the obstruction. These constricting agents constrict the vessels distal of the microvascular bed so that the later applied treatment agents (e.g., clot lysis agents and anti spasmodic agents) are not washed out through the patent microvessels. Thus, the treatment agents may be held in place for a longer period of time. In many cases of MVO, it is suspected that a portion of the microvessels are patent and others are not patent, due to both spasm and thrombosis.

In a similar preferred embodiment, a proximal balloon with negative and positive pressure cycling (as described elsewhere in this specification) can be used to achieve constriction. Microvessels are collapsed under negative pressure and proximal blood is aspirated and replaced during the positive pressure cycle, along with treatment agents including an anti-spasmodic agent and a platelet/thrombus lysing agent.

In another preferred embodiment according to the present invention, the effects of the lytic agents can be augmented by exposure of an ultrasonic field. For example, ultrasonic energy in the frequency range of about 0.5 MHz-10 MHz is produced near a microvascular obstruction, either externally through the skin's surface or internally from a nearby larger vessel. In this respect, the ultrasonic energy radiates to the obstruction, increasing the rate of dissolution of the obstruction by the treatment agents alone.

In another preferred embodiment according to the present invention microvascular obstruction therapy of thrombus dissolution can be assisted by first isolating a vessel enabling pressure to vary independently (barometric isolation), and then cycling the pressure positive and negative at an arbitrary frequency. During the cycling, a lytic solution for the thrombus is introduced, and is driven into the occluding microvessel—thrombus during the positive pressure cycle. In addition, the negative pressure cycle has the tendency to withdraw the thrombus from its micro-vessel. The positive and negative cycling requires a segment of artery to be isolated. This is accomplished by a double balloon technique, or alternatively by a system that blocks proximal and distal flow to the desired region of the vessel.

This technique includes the cessation of antegrade flow, accomplished by a proximal obstructing system, typically balloon that is inflated. The entire system, through its cycling facilitates uptake by the attracting microvessel of a drug or drug combination that is specifically directed toward relieving spasm in the vessel, dissolving the clot, and expanding the vessel around the clock to permit its extraction through the negative pressure cycle.

The use of pressure cycling techniques may include a physical structure that is temporarily placed into an artery while it is being treated. This structure may prevent the vessel from collapsing during implementation of lower than ambient pressure. Preferably, such a device may be a catheter with a mechanical support structure. It may have structural components that are straight, spiral, helical or any other configuration that permits vascular support. It may be self expanding or maybe expendable by a balloon. It may further be a balloon, filled with fluid and capable of supporting the vessel as negative pressures placed on that vessel.

In another preferred embodiment according to the present invention, a gas that is typically quite soluble in blood or water is infused into a vessel to permit access by that vessel of a potent drug. The gas may consist of nitric oxide carbon dioxide or other highly soluble gas. As the gas is infused into the vessel, specifically up to and including regions of thrombus. The bubble may be a carrier for, for example, lytic or anti-spasmodic agents. The bubble concept through utilization of such gases may also clear blood from the field and allow approach of a liquid form of the drug, up to and including the microvasculature.

Myocardial protection during anti-spasmodic therapy and platelet lysis/clot lysis therapy may be followed by a procedure utilizing an agent that is designed to protect heart muscle. The substance may include a cool liquid, at any temperature less than body temperature and can be supplied during or after the treatment procedure. It may also entail, as discussed elsewhere in this specification, agents that cause a rest of the myocardium.

Catheter for Removing Microvascular Obstruction

Figure 2:
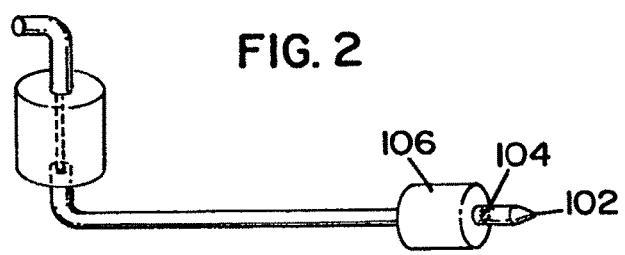
FIG. 2 illustrates a side view of a preferred embodiment of a detection and treatment catheter according to the present invention.

Referring to FIGS. 1 and 2, a single detection and treatment catheter 100 is illustrated according to a preferred embodiment of the present invention. The catheter 100 includes a pressure transducer for detecting a microvascular obstruction, diffusion holes 104 for releasing treatment agents near an obstruction and an occlusion balloon 106 for preventing the treatment agents from moving through the patient's circulatory system. In this respect, the catheter 100 can both detect and treat an obstruction with a single catheter.

More specifically, the catheter 100 senses the location of a microvascular obstruction (e.g., with pressure readings, ultrasound data or other sensor readings). When the obstruction has been located and the distal end of the catheter 100 positioned near the obstruction, the balloon 106 is expanded, creating a sealed area between the obstruction and the balloon 106. Next, the user releases treatment agents through the diffusion holes 104 into the sealed area to begin dissolving the obstruction. The user can continue to monitor the sensor readings (e.g., pressure) to monitor the progress of the obstruction's dissolution. During this process or prior to dissolution of the obstruction, the catheter circulates the fluid within the sealed vascular area and filters out obstruction material (e.g., proteins) and treatment agents, preventing these materials from freely circulating in the patient's vascular system.

Preferably, the catheter 100 includes a guide wire lumen for placement within a patient and may be configured for "single operator exchange".

As previously described, pressure measurement can be used to determine the location of the obstruction and whether the treatment has dissolved or broken up the obstruction.

In one example, a pressure measurement transducer is integrally connected to the agent delivery lumen at either a proximal or distal end of the catheter 100. The pressure may be measured directly to establish the myocardial resistance (pressure divided by flow). In a second example, a distal hole 102 as seen in FIG. 1 opens to a hydraulic column which is further connected to a pressure transducer. In this respect, the catheter 100 includes at least two lumens, one for delivery of the treatment agents and another for the pressure transducer. In a third example, a micromanometer sensor may be disposed at the distal tip of the catheter to obtain a pressure reading.

In a fourth example, pressure is sensed at the distal tip of the catheter by including two or more low pressure balloons that measure the myocardial squeeze that occurs in the myocardium. As the myocardium contracts, it squeezes the microvasculature and typically increases the external pressure on the vessels. As this occurs, the vessels often close during systole in some or even all vessels which allows the pressure in the proximal coronary artery to be sensed over time. If the vessel proximal to the catheter 100 is partially or completely occluded by, for example, a balloon, the pressure in the vessel distal to the balloon and proximal to the myocardium will be sensed as a rhythmic rise in proportion to the myocardial contraction.

If microvascular obstruction is present, this pressure waveform is damped or absent completely, depending on whether the obstruction is complete or not. In this respect there is a comparatively different pressure waveform that is different than when measuring a normal, unobstructed microvasculature. This myocardial contraction will also affect the pressure waveform, dampening it as the "squeeze" reduces as the contracting muscles relax. Similarly, the catheter 100 may be placed in the myocardial venous system and a time-varying pressure waveform introduced to measure pressure from the arterial side. Similarly, the natural waveform generated as the heart muscle contracts can be used in a similar manner as previously described to monitor the obstruction.

The pressure measurements or similar sensor data (e.g., resistance) may be further communicated to the injector system as feedback data. In this respect, the injector system can regulate the treatment agents based on a pressure reading. For example, if the injector system receives pressure readings that are declining, it may reduce the amount of treatment agents being delivered. In another example, the injector system may receive a dramatic drop in pressure readings indicating the obstruction has been dissolved and therefore stops the injection of the treatment agents.

In addition to pressure, flow sensors and flow sensor technology may be used to monitor the injection rate of treatment agents. In one example, flow sensing is performed by monitoring injection rates by tracking a menu displacement transducer that corresponds to a hydraulic driver for fluid (i.e., the treatment agents).

As previously discussed, the occlusion balloon 106 seen in FIGS. 1 and 2 is inflated within a patient's vessel, creating a sealed area that prevents treatment agents from freely moving into the circulatory system and facilitating pressure monitoring. Preferably, the occlusion balloon comprises a soft, compliant material that can be inflated to low pressures to prevent blood flow from entering the vessel.

As seen best in FIG. 1, the diffusion holes 104 are a plurality of small holes in communication with a lumen with in the catheter 100. These holes 104 diffuse the liquid (e.g., treatment agents) that may otherwise create a single jet. These single jets can cause damage to the vessel wall at high flow rates. Preferably, the diffusion holes 104 have a gradient in size or number in proportion to length (e.g., hole size increases in the distal direction) to allow equal drug efflux from all of the holes 104. Similar holes are described in more detail in U.S. Pat. No. 6,949,087, the contents of which are hereby incorporated by reference.

Figure 6:
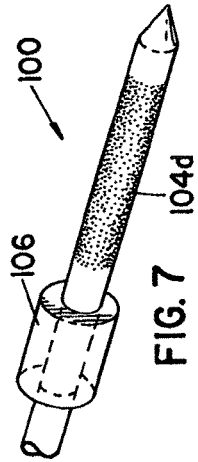
FIG. 6 illustrates a perspective view of another preferred embodiment of a detection and treatment catheter according to the present invention.
Figure 7:
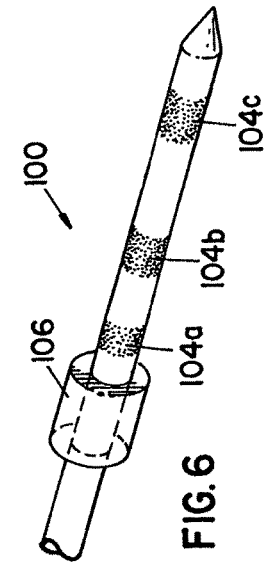
FIG. 7 illustrates a perspective view of another preferred embodiment of a detection and treatment catheter according to the present invention.

As seen in FIG. 6, the catheter 100 may have multiple diffusion hole areas 104A-104C to more diffusely release the treatment agents. Similarly, FIG. 7 illustrates a catheter 100 with a single, elongated diffusion hole region 104D.

Figure 11A:
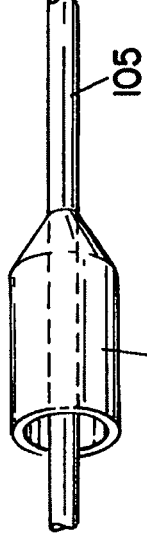
FIGS. 11A-11C illustrates various side views of a catheter tip according to a preferred embodiment of the present invention.
Figure 11B:
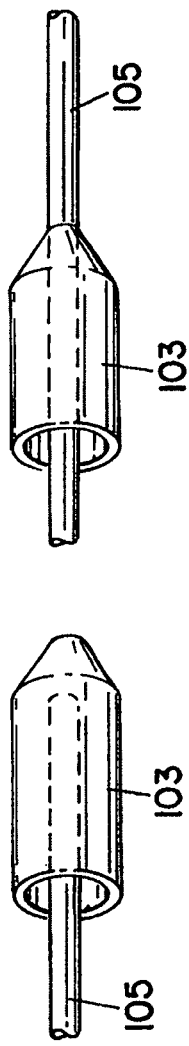
Figure 11C:
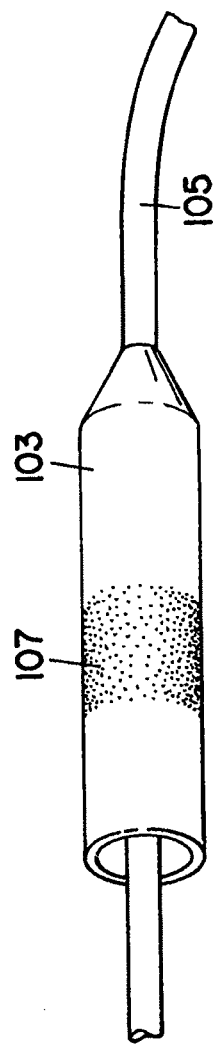

FIGS. 11A-11B illustrate a distal catheter end 103 for the catheter 100 having a virtual distal port which allows the guidewire 105 to pass through, but prevents leakage around the guidewire 105. Instead of an aperture or port, the material of the catheter end 103 grabs the guidewire 105 to create a tight seal. FIG. 11C illustrates a distal catheter end 103 with a virtual distal port and a plurality of diffusion ports 107 for diffusing a treatment agent.

Referring to FIGS. 9 and 10, a double balloon catheter 120 is illustrated which permits distribution of a treatment agent into a short segment of vessel (e.g., artery). This catheter 120 may be particularly useful in the coronary arteries where a branch or branches within a given localized region of heart muscle requires a therapeutic intervention to dispense a treatment agent.

As seen in FIG. 10, the catheter 120 is positioned near a target vessel 132 and within an adjacent vessel 130. Both balloons 106 are inflated, blocking circulation within the adjacent vessel 130 and therefore within the target vessel 132. Once sealed from the greater circulatory system, the diffusion holes 104 release the treatment agent into the target vessel 132 while a pressure port 110 allows the pressure and therefore the obstruction removal progress to be monitored.

The balloons 106 may be connected to the same inflation lumen and therefore inflated simultaneously or can be connected to different inflation lumens to allow for individual inflation. The distance between the two balloons 106 is preferably between 2 mm and 5 cm, but may be more or less depending on the size of the target vessel 132 and the shape of the adjacent vessel 130. As with previously discussed embodiments within this specification, the pressure port 110 connects to a proximal portion of the catheter for sensing pressure. Alternately, a transducer may be positioned within the catheter 120, between the two balloons 106. As with previously discussed embodiments in this specification, additional diagnostic sensors and catheters may be used to determine microvascular integrity, where increased hydraulic resistance indicates significant microvascular obstruction.

Figure 8:
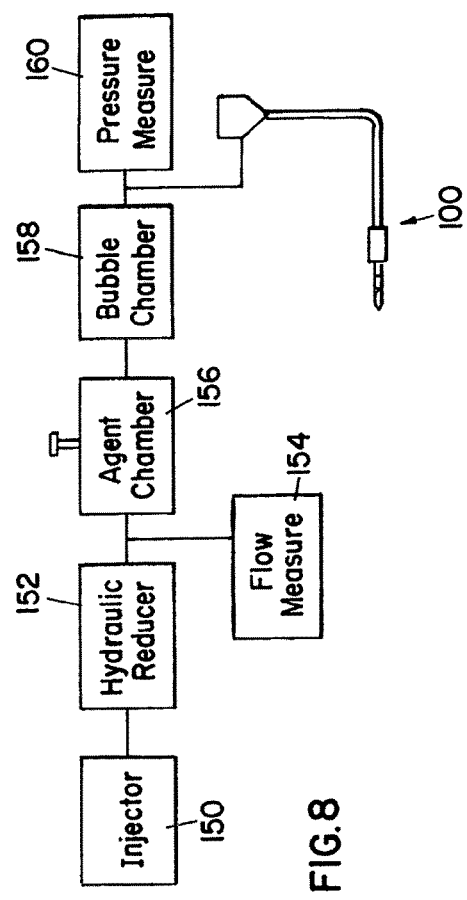
FIG. 8 illustrates a conceptual view of a detection and treatment system according to the present invention.

Referring to FIG. 8, the detection and delivery system preferably includes an injector 150, a hydraulic reducer 152, a flow sensor 154, an agent chamber 156, a bubble chamber 158, and a pressure sensor 160.

Figure 5:
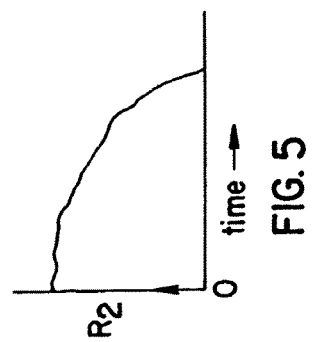
FIG. 5 illustrates an example chart of resistance over time during treatment according to the present invention.

Turning first to the injector 150, this unit drives the injection of the treatment agents. Preferably, the injector is configured to deliver the treatment agents at a constant flow rate which facilitates the accurate measurement of pressure within the system. Such pressure measurement provides a direct analog of distal myocardial or organ resistance/impedance. For example, this resistance/impedance is analogous to two electrical impedances in series. More specifically and as seen in FIG. 4A, a constant flow source provides for a pressure being monitored at a junction point between two impedances. This monitored pressure is directly analogous to the magnitude of the second serial impedance. This resistance (e.g., myocardial resistance) equals the pressure divided by flow, and so can be determined at any point by measuring the pressure when the flow is constant. However, in some situations the flow will not be constant, such as when feedback data is communicated to the injector, and so both pressure and flow must be measured. As seen in FIG. 5, the resistance will drop as the treatment agents remove the obstruction.

Figure 4B:
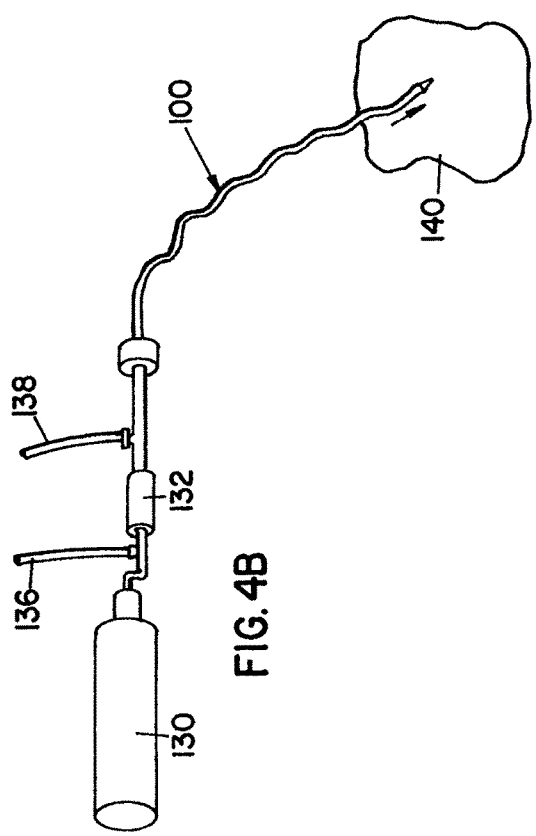
FIG. 4B illustrates a pressure measurement system according to a preferred embodiment of the present invention.
Figure 4A:
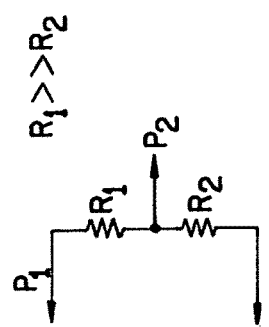
FIG. 4A illustrates a conceptual diagram of pressure measurements according to a preferred embodiment of the present invention.

In an alternate example, FIG. 4B illustrates a catheter 100 with a plugged distal port for measuring microvascular resistance. A flow pump 130 provides a constant flow source to the catheter 100 near the microvasculature 140 and pressure measurements are taken at a location 136 proximal to a fixed resistance 132 and a location 138 distal to the fixed resistance 132. Distal flow is calculated from the pressure differential across the proximal resistance 132 and the known, fixed infusion rate. Pressure at the catheter infusion tip is a surrogate for microvascular resistance and is measurable in real time.

Turning next to the hydraulic reducer 152, this unit enables driving the system from a drug and/or contrast standpoint with a proximal inlet port. The hydraulic reducer comprises a linear ram of different diameters, such that comparable linear displacement yields a fixed volume reduction in proportion to the relative areas of the hydraulic ram. Further details of hydraulic reducer technology can be seen in U.S. Patent Publication Number 2005-0165354, the contents of which are hereby incorporated by reference.

Turning next to the agent chamber 156, this unit contains and distributes the treatment agents that are pushed through a bubble detection chamber 158, past a pressure transducer 160 (for measuring pressure of the fluid), and through the catheter 100 and into the vessel of the patient.

Preferably, real time impedance readings are calculated during a procedure which allows a user to monitor the removal progress of the obstruction. Thus, as treatment is infused from the catheter diffusion holes 104, the effect of the treatment can be immediately observed by a myocardial impedance drop (e.g., a pressure drop if flow remains constant since impedance is pressure divided by flow).

Since the treatment agent is delivered in a fluid form through the diffusion holes 104, the treatment agent and its delivery passages can be used to monitor both the flow and pressure readings needed to calculate impedance, as seen in FIG. 8. Additionally, the impedance of the system may be increased to produce more sensitive detection of the obstruction. For example, higher impedance may be achieved by including smaller inlet ports at locations prior to the catheter 100 or a small bladder lumen in the catheter itself which becomes integral in providing a constant flow source and may be further augmented by including a small diameter port that feeds fluid into the system. Measuring absolute volume injected and the rate of that line of injection via methods such as time differentiation/time derivative will give an accurate estimation of flow. Utilization of the flow parameter in conjunction with pressure will calculate myocardial impedance or distal organ impedance.

Figure 3:
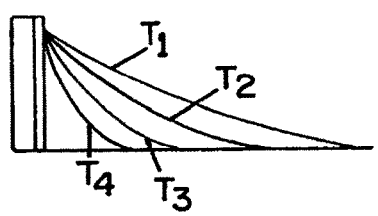
FIG. 3 illustrates example pressure reading from pressure bleeds relating to a microvascular obstruction.

Alternately, the presence and degree of the obstruction can be calculated by creating a pressure head at the origin of the vessel and measuring the "bleed off" of pressure, as seen in FIG. 3. This can lead to a first or second order exponential decrease in standard parameters such as "Tau" which can be calculated so as to directly determine the presence and degree of vessel obstruction. Tau is an exponential constant commonly used in a decreasing parameter system.

In another preferred embodiment, a second simultaneous pressure reading taken at a location proximal to the main distal pressure reading (e.g., from a port proximal to the diffusion holes 104) can be obtained, allowing the two pressures to be compared. The second pressure reading can provide a strong analog to the distal impedance and therefore better identify and quantify the obstruction. Similarly, the system may include multiple pressure sensors (e.g., transducers) on the same fluid line to obtain a more accurate pressure reading.

As previously discussed, the delivery catheter may produce ultrasound energy in addition to treatment agents to more quickly dissolve an obstruction. For example, catheters produced by the EKOS Corporation such as the EKOS Lysus Peripheral Infusion System can be used for this purpose and further modified to include additional features described in this specification, such as pressure and flow sensing. The ultrasound energy is thought to make fibrin more accessible to the treatment agents while driving the treatment agents into the obstruction. Further, the ultrasound energy may allow the treatment agents to be delivered through tissue layers within the patient such as the adventitia.

The delivery catheter may also produce ultrasound energy for imaging and detection (e.g., using a Doppler analysis) as previously described in this specification.

One preferred embodiment of the present invention includes treating a microvascular obstruction comprising locating a position of said microvascular obstruction within a vasculature of a patient; advancing a distal end of a treatment catheter through said vasculature and within proximity of said position of said microvascular obstruction; expanding an occlusion member within said vasculature; delivering a treatment agent between said expanding occlusion member and said microvascular obstruction; and monitoring treatment of said microvascular obstruction.

Alternately in this preferred embodiment, said locating a position of said microvascular obstruction within a vasculature of a patient is selected from a group of: magnetic resonance imaging, ultrasound imaging, pressure measurement, vascular impedance measurement and phasic flow measurement.

Alternately in this preferred embodiment, said expanding an occlusion member within said vasculature further comprises expanding a second occlusion member within said vasculature.

Alternately in this preferred embodiment, said expanding an occlusion member within said vasculature further comprises inflating an occlusion balloon.

Alternately in this preferred embodiment, said delivering a treatment agent between said expanding occlusion member and said microvascular obstruction further comprises delivering one or more treatment agents selected from the following group: Factor X, Factor VII, a IIB/IIIA agent, Tick Anticoagulant Peptide, echistatin, Integrilin, PPACK, DPG peptide inhibitor, TNK, streptokinase, urokinase, rTPA, adenosine, nitroglycerin, sodium nitroprusside, nicorandil, Hirulog, Bivalrudin, ReoPro, eptifibatide, TAP, Heparins, LMW Heparins, Argatroban, Hirudin, Refludan/Lepirudin (Berlex), Desirudin, recombinant forms, ABCIXIMAB, Eptifibatide, Tirofiban, Alteplase, Reteplase, Tenecteplase, Factor Xz, rivaroxaban, Fodaparinux, adenosine, anti-PMN antibodies, anti-leukocyte antibodies, quinolone agents, nitrogen mustard, hydroxyurea, anti-serotonin agents, such as cinanserin, pizotifen, cyproheptadine, lysenyl, mianserin, methysergide, promethazine, octreotide, trypsin, papain, chymotrypsin, lidocaine, quinidine, amiodarone, procainamide, propofenone, and beta blockade.

Alternately in this preferred embodiment, said delivering a treatment agent between said expanding occlusion member and said microvascular obstruction further comprises disbursing said treatment agent through diffusion apertures of said catheter.

Alternately in this preferred embodiment, said disbursing said treatment agent through diffusion apertures of said catheter further comprises disbursing said treatment agent through a diffusion aperture region have a size gradient of said diffusion apertures.

Alternately in this preferred embodiment, wherein said monitoring treatment of said microvascular obstruction further comprises measuring myocardial resistance.

Alternately in this preferred embodiment, wherein said measuring myocardial resistance further comprises measuring flow and pressure of a fluid supplied between said expanding occlusion member and said microvascular obstruction.

Another preferred embodiment of the present invention includes a method for treating an obstruction of a microvascular vessel within a patient, comprising advancing a distal end of a guidewire to a location in communication with said obstruction; advancing a distal end of said treatment catheter over said guidewire to said location in communication with said obstruction; releasing a treatment agent from said treatment catheter; monitoring an impedance of said microvascular vessel; stopping said releasing of said treatment agent when said impedance indicates removal of said obstruction.

Alternately in this preferred embodiment, said monitoring an impedance of said microvascular vessel comprises determining an impedance by dividing a flow measurement of said treatment agent by a pressure measurement of a location in communication with said microvascular vessel.

Alternately in this preferred embodiment, said flow measurement comprises measuring a pressure differential between a fixed resistance in communication with said microvascular vessel.

Alternately in this preferred embodiment, said pressure measurement of a location in communication with said microvascular vessel is measured with a pressure transducer coupled to said treatment catheter.

Alternately in this preferred embodiment, further comprising exposing said obstruction to ultrasonic energy.

Another preferred embodiment of the present invention includes a system for treating a microvascular obstruction comprising: a treatment catheter comprising: an expandable occlusion balloon disposed on a distal end of said treatment catheter; a first lumen; a plurality of diffusion holes in communication with said first lumen and located at said distal end of said treatment catheter; and a selectively expandable occlusion member disposed at said distal end of said treatment catheter; an injector in communication with said first lumen for delivering a treatment agent through said catheter; and, an occlusion sensor for monitoring a level of blockage by said occlusion.

Alternately in this preferred embodiment, said treatment catheter further comprises a second selectively expandable occlusion member.

Alternately in this preferred embodiment, said occlusion sensor comprises a pressure port at said distal end of said treatment catheter.

Alternately in this preferred embodiment, said occlusion sensor comprises a pressure transducer at said distal end of said treatment catheter.

Alternately in this preferred embodiment, said occlusion sensor comprises a flow sensor coupled to said first lumen.

Alternately in this preferred embodiment, said flow sensor comprises a first pressure sensor and a second pressure sensor in communication with said first lumen for measuring a pressure differential of a resistance member having a fixed resistance.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for treating a thrombotic or spasmodic obstruction in microvasculature with a treatment agent, the system comprising:
    an injector;
    an expandable occlusion member;
    an intravascular treatment catheter at least partially surrounded by the expandable occlusion member, the intravascular treatment catheter comprising a proximal portion in fluid communication with the injector, said intravascular treatment catheter comprising at least two lumens in communication with the proximal portion, and a distal diffusion portion, wherein the at least two lumens comprise:
- a first lumen configured to deliver inflation medium from the proximal portion of the intravascular treatment catheter to the expandable occlusion member disposed at a distal portion of the intravascular treatment catheter so as to selectively inflate and deflate the expandable occlusion member, said expandable occlusion member being positioned proximal to the distal diffusion portion of the intravascular treatment catheter; and
- a second lumen configured to fluidly communicate delivery of the treatment agent from the injector to the distal diffusion portion of the treatment catheter, said distal diffusion portion defining a plurality of small holes located distally of the expandable occlusion member, and configured to diffuse the treatment agents into the vasculature;

wherein the distal tip of the intravascular treatment catheter comprises a distal port in communication with the second lumen to allow passage of a guidewire to position the intravascular catheter in the vasculature, said distal port being configured to allow passage of the guidewire through the distal tip, but sufficiently restrict the injection of treatment agent out of the distal port; and a sensor for monitoring the status of thrombotic or spasmodic occlusion of the microvasculature.

2. The system of claim 1, wherein the plurality of small holes are configured so as to allow infusion and extraction of medium and a thrombotic material therethrough.

3. The system of claim 1, wherein the sensor comprises a distal port at said distal portion of the treatment catheter.

4. The system of claim 1, wherein the sensor comprises a pressure transducer at the distal portion of the intravascular treatment catheter.

5. The system of claim 1, wherein the at least two lumens include a third lumen, wherein the third lumen contains a proximal sensor configured to measure a pressure or a flow from the distal portion of the intravascular treatment catheter to a proximal portion of the intravascular treatment catheter.

6. The system of claim 1, wherein the sensor comprises a flow sensor.

7. The system of claim 1, wherein the sensor comprises an ultrasonic sensor.

8. The system of claim 1, further comprising an ultra sound emitter configured to facilitate a dissolution of the thrombotic or spasmodic obstruction.

9. The system of claim 1, further comprising the guide wire.

* * * * *